United States Patent
Chen et al.

(10) Patent No.: US 8,273,828 B2
(45) Date of Patent: Sep. 25, 2012

(54) METHODS FOR INTRODUCING REACTIVE SECONDARY AMINES PENDANT TO POLYMERS BACKBONES THAT ARE USEFUL FOR DIAZENIUMDIOLATION

(75) Inventors: Mingfei Chen, Santa Rosa, CA (US); Peiwen Cheng, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 636 days.

(21) Appl. No.: 11/782,146

(22) Filed: Jul. 24, 2007

(65) Prior Publication Data

US 2009/0028966 A1    Jan. 29, 2009

(51) Int. Cl.
C08F 8/30       (2006.01)
C08F 8/32       (2006.01)
C08L 63/00      (2006.01)
A61L 31/04      (2006.01)

(52) U.S. Cl. .................. 525/327.3; 525/330.5; 525/379; 525/381; 525/382; 525/523; 424/423; 424/486; 424/487; 424/78.19; 424/78.27; 424/78.38; 623/1.15; 623/1.42

(58) Field of Classification Search ............... 525/327.3, 525/330.5, 379, 381, 382, 523; 424/78.19, 424/78.27, 78.38, 423, 486, 487; 623/1.15, 623/1.42
See application file for complete search history.

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,155,137 A | 10/1992 | Keefer et al. |
| 5,212,204 A | 5/1993 | Keefer et al. |
| 5,250,550 A | 10/1993 | Keefer et al. |
| 5,268,465 A | 12/1993 | Bredt et al. |
| 5,362,718 A | 11/1994 | Skotnicki et al. |
| 5,366,997 A | 11/1994 | Keefer et al. |
| 5,380,758 A | 1/1995 | Stamler et al. |
| 5,405,919 A | 4/1995 | Keefer et al. |
| 5,428,070 A | 6/1995 | Cooke et al. |
| 5,468,630 A | 11/1995 | Billiar et al. |
| 5,525,357 A | 6/1996 | Keefer et al. |
| 5,574,068 A | 11/1996 | Stamler et al. |
| 5,583,101 A | 12/1996 | Stamler et al. |
| 5,650,447 A | 7/1997 | Keefer et al. |
| 5,658,565 A | 8/1997 | Billiar et al. |
| 5,665,077 A | 9/1997 | Rosen et al. |
| 5,718,892 A | 2/1998 | Keefer et al. |
| 5,891,459 A | 4/1999 | Cooke et al. |
| 5,900,246 A | 5/1999 | Lambert |
| 5,945,452 A | 8/1999 | Cooke et al. |
| 6,015,815 A | 1/2000 | Mollison |
| 6,110,453 A | 8/2000 | Keefer et al. |
| 6,153,588 A | 11/2000 | Chrzan et al. |
| 6,290,981 B1 | 9/2001 | Keefer et al. |
| 6,329,386 B1 | 12/2001 | Mollison |
| 6,403,759 B2 | 6/2002 | Stamler et al. |
| 6,610,660 B1 | 8/2003 | Saavedra et al. |
| 6,673,891 B2 | 1/2004 | Stamler et al. |
| 6,706,274 B2 | 3/2004 | Herrmann et al. |
| 6,737,447 B1 | 5/2004 | Smith et al. |
| 6,759,430 B2 | 7/2004 | Anggard et al. |
| 6,841,166 B1 | 1/2005 | Zhang et al. |
| 6,875,840 B2 | 4/2005 | Stack et al. |
| 6,911,478 B2 | 6/2005 | Hrabie et al. |
| 6,949,530 B2 | 9/2005 | Hrabie et al. |
| 6,951,902 B2 | 10/2005 | McDonald et al. |
| 7,070,798 B1 | 7/2006 | Michal et al. |
| 7,087,709 B2 | 8/2006 | Stamler et al. |
| 7,105,502 B2 | 9/2006 | Arnold et al. |
| 7,378,105 B2 | 5/2008 | Burke et al. |
| 2002/0094985 A1 | 7/2002 | Herrmann et al. |
| 2004/0037836 A1 | 2/2004 | Stamler et al. |
| 2004/0171589 A1 | 9/2004 | Herrmann et al. |
| 2004/0180131 A1 | 9/2004 | Cheng |
| 2005/0171596 A1 | 8/2005 | Furst et al. |
| 2005/0203069 A1 | 9/2005 | Arnold et al. |
| 2005/0265958 A1 | 12/2005 | West et al. |
| 2005/0281866 A1 | 12/2005 | Jarrett et al. |
| 2006/0008529 A1 | 1/2006 | Meyerhuff et al. |
| 2006/0099235 A1 | 5/2006 | Blakstvedt et al. |
| 2006/0121089 A1 | 6/2006 | Michal et al. |
| 2006/0195142 A1 | 8/2006 | Shalaby |
| 2006/0251824 A1 | 11/2006 | Boulais et al. |
| 2007/0014828 A1 | 1/2007 | Fitzhugh et al. |
| 2007/0053952 A1 | 3/2007 | Chen et al. |
| 2007/0185561 A1 | 8/2007 | Schmitz et al. |
| 2007/0264225 A1 | 11/2007 | Cheng et al. |
| 2008/0220040 A1 | 9/2008 | Cheng et al. |
| 2009/0222088 A1 | 9/2009 | Chen et al. |
| 2009/0232863 A1 | 9/2009 | Cheng et al. |
| 2009/0232868 A1 | 9/2009 | Chen et al. |

FOREIGN PATENT DOCUMENTS

EP          0945148          9/1999
(Continued)

OTHER PUBLICATIONS

Washington State University, Chemistry 240, Summer 2001 online lecture notes, "Amines—Reactions", pp. 1-5.*
Parzuchowski et al., J. Amer. Chem. Soc. 124 (2002) 12182-12191.*
Liu et al., J. Colloid and Interfacial Science 303 (2006) 99-108.*
Tashiro et al., "Removal of Methyl Orange by Systems of Insoluble Poly(glycidyl methacrylate)—g—Tetraethylene-Pentamine and—g—Polyethyleneimines"Angewandte makromolekulara Chemie. Applied Macromolecularchemistry and Physics, Wiley Vch, Weinheim, DE, vol. 205, Feb. 1, 1993, pp. 31-45.
Reynolds et al., "Nitric Oxide Releasing Polyurethanes with Covalently Linked Diazeniumdiolated Secondary Amines" Biomacromolecules, Acs, Washington DC, vol. 7, Feb. 25, 2006, pp. 987-994.
U.S. Appl. No. 12/340,089, filed Dec. 19, 2008.
U.S. Appl. No. 12/422,425, filed Apr. 13, 2009.
Hrabie et al., "New Nitric Oxide-Releasing Zwitterions Derived from Polyamines" J. Org. Chem, 1993, 58, 1472-1476.

(Continued)

Primary Examiner — Roberto Rabago

(57) ABSTRACT

Biocompatible polymers having polymer backbones with at least one secondary amine suitable for diazeniumdiolation are disclosed. Specifically, methods for providing secondary amines-containing polymers using epoxide-opening reactions are provided. More specifically, nitric oxide-releasing medical devices made using these polymers are disclosed.

14 Claims, 1 Drawing Sheet

FOREIGN PATENT DOCUMENTS

| | | |
|---|---|---|
| EP | EP0992252 | 4/2000 |
| EP | 1300424 | 4/2003 |
| WO | WO96/15797 | 5/1996 |
| WO | WO99/01427 | 1/1999 |
| WO | WO01/10344 | 2/2001 |
| WO | WO2005/039664 | 5/2005 |
| WO | WO95/24908 | 9/2005 |
| WO | WO2005/081752 | 9/2005 |
| WO | WO2006/037105 | 4/2006 |
| WO | WO2007/024501 | 3/2007 |
| WO | WO2007/053292 | 5/2007 |
| WO | WO2007/053578 | 5/2007 |

OTHER PUBLICATIONS

Drago et al., "The Reaction of Notrogen(II) Oxide with Diethylamine" Contribution from the W.A. Noyes Laboratory, University of Illinois, Jun. 24. 1959.

Parzuchowski et al., "Synthesis of Potentially More Blood Compatible Nitric Oxide Releasing Acrylic Copolymers" Polymer Preprints, 2001. 42(1), pp. 448-449.

Williams et al. "Nitric Oxide-Releasing Nonsteroidal Anti-Inflammatory Drugs (NSAIDs) Alter the Kinetics of Human Colon Cancer Cell Lines More effectively then Traditional NSAIDs: Implications for Colon Cancer Chemoprevention" Cancer Research, 61, 3285-3289, Apr. 15, 2001, pp. 3285-3289.

Frost et al, "Polymers Incorporating Nitric Oxide Releasing/Generating Substances for improved Biocompatibility of Blood-Contacting Medical Devices" Biomaterials 26 (2005) 1685-93.

Deng et al., "Polymerization of Lactides and Lactones 11. Ring-Opening Polymerization of x-Acetyl-y-Butyrolactone and Copolymerization with B-Butyrolactone" European Polymer Journal, 36 (2000) 2739-2741.

Lovric et al., "Scope and Limitations of Sodium and Potassium Trimethylsilanolate as Reagents fro Conversion of Esters to Carboxylic Acids" Croatica Chemica Acta, CCACAA 80 (1), 109-115 (2007).

Kireev et al., "Polymerization of Methyl Methacrylate and Vinyl Acetate Initiated by the Manganese Carbonyl-1,2-Epoxy-4,4,4-Trichlorobutance System" Polymer Science, Ser. B, 2006, vol. 48. Nos. 5-6, pp. 138-141.

Liu et al., "Dethylenetriamine-Grafted Poly(Glycidyl Methacrylate) Adsorbent for Effective Copper Ion Adsorption" Journal of Colloid and Interface Science 303 (2006) 99-108.

Oh et al., "Spontaneous Catalytic Generation of Nitric Oxide from S-Nitrosothiols at the Surface of Polymer Films Doped with Lipophilic Copper (II) Complex" J. Am. Chem. Soc. 203, 125, pp. 9552-9553, 2003.

Abizaid, Alexandre MD "Novel Approaches to New DES Therapies: Where are we Going?" ACC 2007, New Orleans.

Pasterkamp et al., "Atherosclerotic Plaque Rupture: an Overview" J Clin Basic Cardiol, 2000 3: pp. 81-96.

Wolfe et al., "Cyclic Hydroxamates, Especially Muitiply Substituted [1,2] Oxazinan-3-Ones" Cna, J. Chem. 81: 937-960 (2003).

U.S. Appl. No. 11/383,257, filed May 15, 2006, Chen, Peiwin.

U.S. Appl. No. 12/049,618, filed May 15, 2000, Chen, Peiwin.

U.S. Appl. No. 12/049,648, filed Mar. 17, 2008, Chen, Mingfei.

Washington State Univ. Lecture, Chemistry 240, Summer 2001, http://chemistry2.csudh.edu/rpendarvis/aminrxn.html.

* cited by examiner

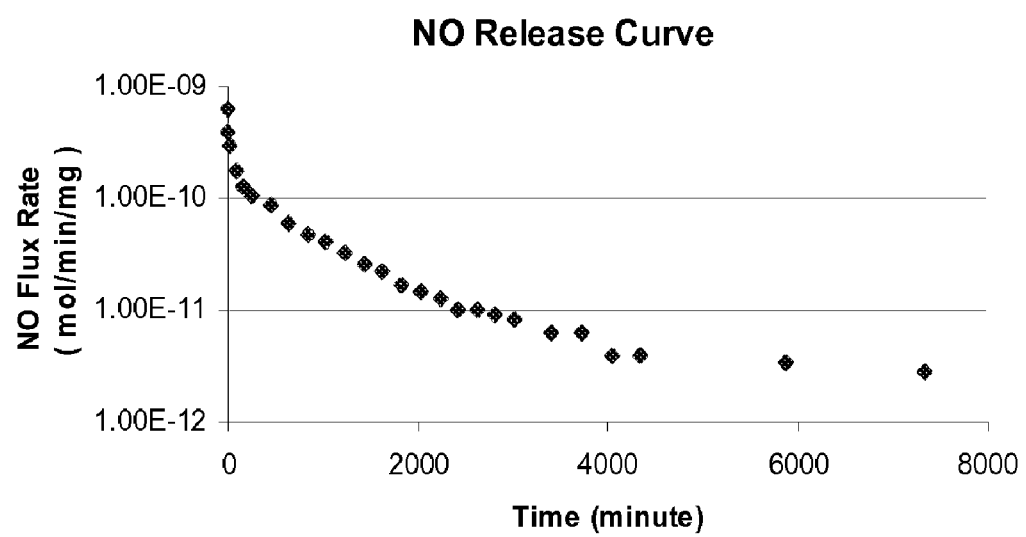

METHODS FOR INTRODUCING REACTIVE SECONDARY AMINES PENDANT TO POLYMERS BACKBONES THAT ARE USEFUL FOR DIAZENIUMDIOLATION

FIELD OF THE INVENTION

The present invention relates to epoxide-derived nitric oxide (NO) donating polymers for fabricating and coating medical devices.

BACKGROUND OF THE INVENTION

Nitric oxide (NO) is a simple diatomic molecule that plays a diverse and complex role in cellular physiology. Less than 25 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOSI, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{2+}$ levels. Increased intracellular $Ca^{2+}$ concentrations result in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Medical research is rapidly discovering therapeutic applications for NO including the fields of vascular surgery and interventional cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate over-proliferation of vascular smooth muscle cells during the healing process, restricting or occluding the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administered L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis an inhibitory therapeutic such as NO must be administered for a sustained period at therapeutic levels. Consequently, any NO-releasing medical device used to treat restenosis must be suitable for implantation. An ideal candidate device is the vascular stent. Therefore, a stent that safely provides therapeutically effective amounts of NO to a precise location would represent a significant advance in restenosis treatment and prevention.

Nitric oxide-releasing compounds suitable for in vivo applications have been developed by a number of investigators. As early as 1960 it was demonstrated that NO gas could be reacted with amines, for example, diethylamine, to form NO-releasing anions having the following general formula R—R'N—N(O)NO. Salts of these compounds could spontaneously decompose and release NO in solution.

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 all of which are herein incorporated by reference.

The in vivo half-life of NO, however, is limited, causing difficulties in delivering NO to the intended area. Therefore NO-releasing compounds which can produce extended release of NO are needed. Several exemplary NO-releasing compounds have been developed for this purpose, including for example a NO donating aspirin derivative, amyl nitrite and isosorbide dinitrate. Additionally, biocompatible polymers having NO adducts (see, for example, U.S. Patent Publications 2006/0008529 and 2004/0037836) and which release NO in a controlled manner have been reported.

Secondary amines have the ability to bind two moles of NO and release them in an aqueous environment. The general structure of exemplary secondary amines capable of binding two NO molecules is depicted in Formula 1, referred to hereinafter a diazeniumdiolate, (wherein M is a counterion, and can be a metal, with the appropriate charge, or a proton and wherein $R^1$ and $R^2$ are generic notation for organic and inorganic chemical groups). Exposing secondary amines to basic conditions while incorporating NO gas under high pressure leads to the formation of diazeniumdiolates.

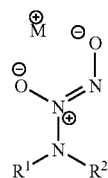

Formula 1

SUMMARY OF THE INVENTION

The present invention provides nitric oxide (NO) donating polymers suitable for fabricating and coating medical devices. More specifically, the present invention provides epoxide-derived polymers comprising at least one secondary amine that can be diazeniumdiolated to release or donate NO controllably in a physiological environment. Furthermore, a method for the synthesis of polymers comprising secondary amines from epoxides is disclosed.

In one embodiment of the present invention, a method of providing a polymer with at least one reactive secondary amine is disclosed comprising (a) providing a polymer having epoxide pendant groups; (b) reacting the polymer with a compound having the general formula $R^2$—$NH_2$; wherein $R^2$ is selected from the group consisting of $C_1$ to $C_{20}$ straight chain alkyls, $C_3$ to $C_{20}$ cycloalkyls, $C_2$ to $C_{20}$ alkenyls, $C_2$ to $C_{20}$ alkynyls, $C_2$ to $C_{14}$ heteroatom substituted alkyls, $C_2$ to $C_{14}$ heteroatom substituted cycloalkyls, $C_1$ to $C_{10}$ multiple amine containing hydrocarbons, $C_4$ to $C_{10}$ substituted aryls and $C_4$ to $C_{10}$ substituted heteroatom substituted heteroaryls under conditions wherein a secondary amine is formed; and (c) reacting the secondary amine with NO under pressure to form a diazeniumdiolate thereof.

In another embodiment of the present invention, a method of providing a monomer with at least one reactive secondary amine is disclosed comprising (a) providing a polymerizable first monomer having the general structure of Formula 2:

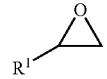

Formula 2 wherein $R^1$ is a polymerizable moiety selected from the group consisting of acrylates, methacrylates, lactones, $C_2$ to $C_{20}$ alkenyls and $C_2$ to $C_{20}$ alkynyls; (b) reacting the first monomer with a compound having the general formula $R^2$—$NH_2$; wherein $R^2$ is selected from the group consisting of $C_1$ to $C_{20}$ straight chain alkyls, $C_3$ to $C_{20}$ cycloalkyls, $C_2$ to $C_{20}$ alkenyls, $C_2$ to $C_{20}$ alkynyls, $C_2$ to $C_{14}$ heteroatom substituted alkyls, $C_2$ to $C_{14}$ heteroatom substituted cycloalkyls, $C_1$ to $C_{10}$ multiple amine containing hydrocarbons, $C_4$ to $C_{10}$ substituted aryls and $C_4$ to $C_{10}$ substituted heteroatom substituted heteroaryls under conditions wherein a monomer having a reactive secondary amine according to the general structure of Formula 3 is formed.

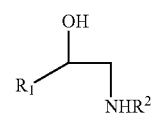

Formula 3

In another embodiment of the present invention, reaction step (b) further comprises a catalyst selected from the group consisting of $LiClO_4$, mineral acids, Bronsted acids, ion exchange resins, zeolites, oxophilic metals, proton sponges, buffer solutions, alkali earth metals, alkaline earth metals, transition metals, and organometallic compounds.

In another embodiment, the $C_1$ to $C_{10}$ multiple amine-containing hydrocarbon is selected from the group consisting of N-methylethylenediamine, N-methylproplenediamine, N-methylbutylenediamine, N-ethytethytenediamine, N-ethylpropylenediamine, N-ethylbutylenediamine, N-benzylethylenediamine, N-benzylpropylytenediamine, N-benzylpropylenediamine, N-propylethylenediamine, N-propylpropylenediamine, N-propylbutylenediamine, ethylenediamine, diethylenetriamine, triethylenetetramine, tetraethylenepentamine and pentaethylenehexamine.

In another embodiment of the method of providing a polymer with reactive secondary amines, the polymer is selected from the group consisting of polyethers, vinyl polymers such as poly methacrylates, poly acrylates, polystyrene and poly (vinyl chloride), polycarbonate, polyurethane and polyesters. In another embodiment, the polymer is comprised of monomers selected from the group consisting of methyl methacrylate, ethyl methacrylate, propyl methacrylate, butyl methacrylate, pentyl methacrylate, hexyl methacrylate, heptyl methacrylate, octyl methacrylate, dodecyl methacrylate, 2-(ethoxy ethyl methacrylate), glycidyl methacrylate, poly (ethylene glycol) methacrylate, methyl acrylate, ethyl acrylate, propyl acrylate, butyl acrylate, pentyl acrylate, hexyl acrylate, heptyl acrylate, octyl acrylate, dodecyl acrylate, 2-ethoxyethyl acrylate, glycidyl acrylate, poly(ethylene glycol) acrylate, ε-caprolactone, polyethylene glycol (PEG), trimethylene carbonate, lactide, glycolide, N-acetyl 4-aza-caprolactone, cyclohexyl caprolactone, 4-tert-butyl caprolactone and the caprolactone of Formula 4.

In one embodiment of the present invention, a method of providing NO donating polymers is disclosed comprising (a) providing a polymer comprising monomers having at least one reactive secondary amine; and (b) reacting said secondary amine with NO under pressure to form a diazeniumdiolate thereof.

In another embodiment of the present invention, a medical device is provided comprising a polymer prepared according to the methods of the present invention. In another embodiment, the medical device comprises a vascular stent.

In one embodiment, a medical device is provided comprising a polymer coating wherein the polymer is prepared according to the methods of the present invention. In another embodiment the medical device comprises a vascular stent.

In another embodiment of the present invention, the polymer further comprises at least one drug selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, NO, bisphosphonates, epidermal growth factor inhibitors, antibodies, proteasome inhibitors, antibiotics, anti-inflammatories, anti-sense nucleotides and transforming nucleic acids. In another embodiment, the drug comprises at least one compound selected from the group consisting of sirolimus (rapamycin), tacrolimus (FK506), everolimus (certican), temsirolimus (CCI-779) and zotarolimus (ABT-578). In yet another embodiment, the drug is zotarolimus.

DEFINITION OF TERMS

Lactide: As used herein, lactide refers to 3,6-dimethyl-1,4-dioxane-2,5-dione. More commonly lactide is also referred to herein as the heterodimer of R and S forms of lactic acid, the homodimer of the S form of lactic acid and the homodimer of the R form of lactic acid. Lactic acid and lactide are used interchangeably herein. The term dimer is well known to those ordinarily skilled in the art.

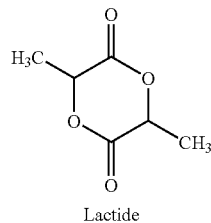

Lactide

Glycolide: As used herein, glycolide refers to a molecule having the general structure:

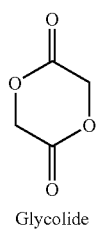

Glycolide 4-tert-butyl caprolactone: As used herein, 4-tert-butyl caprolactone refers to a molecule having the general structure:

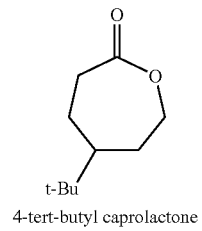

4-tert-butyl caprolactone

N-acetyl 4-aza-caprolactone: As used herein, N-acetyl 4-aza-caprolactone refers to a molecule having the general structure:

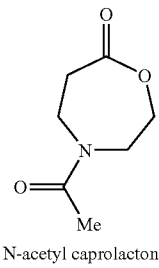

N-acetyl caprolactone

Backbone: As used herein, "backbone" refers to the main chain of a polymer or copolymer of the present invention. A "polyester backbone" as used herein refers to the main chain of a biodegradable polymer comprising ester linkages.

Bioactive Agent: As used herein "bioactive agent" shall include any drug, pharmaceutical compound or molecule having a therapeutic effect in an animal. Exemplary, non-limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARy), hypothemycin, NO, bisphosphonates, epidermal growth factor inhibitors, antibodies, proteasome inhibitors, antibiotics, anti-inflammatories, anti-sense nucleotides, and transforming nucleic acids. Bioactive agents can also include cytostatic compounds, chemotherapeutic agents, analgesics, statins, nucleic acids, polypeptides, growth factors, and delivery vectors including, but not limited to, recombinant microorganisms, and liposomes.

Exemplary FKBP 12 binding compounds include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid) and zotarolimus (ABT-578). Additionally, and other rapamycin hydroxyesters may be used in combination with the polymers of the present invention.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Copolymer: As used herein, a "copolymer" is a macromolecule produced by the simultaneous chain addition polymerization of two or more dissimilar units such as monomers. Copolymers include bipolymers (two dissimilar units), terpolymers (three dissimilar units), etc.

Controlled release: As used herein, "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Diazeniumdiolate: As used herein, "diazeniumdiolate" refers to a class of nitric oxide donating molecules, also referred to as NONOates (1-substituted diazen-1-ium-1,2-diolates) are chemical species that carry the [N(O)NO]— functional group and release nitric oxide (NO) molecules under physiological conditions at a predictable rate. Furthermore, "diazeniumdiolated" or "diazeniumdiolation" refers to molecules having diazeniumdiolate groups or the process of adding such groups to a polymer.

Glass Transition Temperature ($T_g$): As used herein, "glass transition temperature" or "$T_g$" refers to a temperature wherein a polymer structurally transitions from a elastic pliable state to a rigid and brittle state.

Glycidyl Methacrylate: As used herein, glycidyl methacrylate refers to a molecule having the general structure:

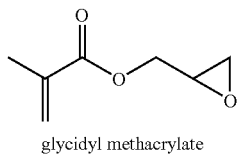

glycidyl methacrylate $M_n$: As used herein, $M_n$ refers to number-average molecular weight. Mathematically it is represented by the following formula:

$$M_n = \sum_i N_i M_i \Big/ \sum_i N_i,$$

wherein the $N_i$ is the number of moles whose weight is $M_i$.

$M_w$: As used herein, $M_w$ refers to weight average molecular weight that is the average weight that a given polymer may have. Mathematically it is represented by the following formula:

$$M_w = \sum_i N_i M_i^2 \Big/ \sum_i N_i M_i,$$

wherein $N_i$ is the number of molecules whose weight is $M_i$.

BRIEF DESCRIPTION OF THE DRAWINGS

FIG. 1 is a nitric oxide release curve referred to in Example 7.

DETAILED DESCRIPTION OF THE INVENTION

Polymers containing secondary amines having nitric oxide (NO) molecules incorporated therein have been synthesized and diazeniumdiolates formed. Increasing the numbers of secondary amines in the polymers provides for increased NO loading, more stable diazeniumdiolates and enhances the prospect of more finely tuned controlled release. Applicants have determined that biocompatible polymers based on epoxide-opening reactions with primary amines provide NO-donating polymers suitable for fabricating and coating medical devices.

The present invention provides epoxide-derived NO donating polymers suitable for fabricating and coating medical devices. More specifically, the present invention provides polymers comprising side chains having at least one epoxide-derived secondary amine that can be diazeniumdiolated to release or donate NO controllably in a physiological environment. Furthermore, a method for the synthesis of epoxide-derived polymers comprising secondary amines from epoxides is disclosed.

The polymers of the present invention comprise homopolymers and copolymers. The homopolymers consist of monomer units comprising at least one secondary amine group on each side chain. The polymers of the present invention include, but are not limited to poly methacrylates, poly acrylates, polystyrene, poly(vinyl chloride), polyesters, polycarbonates, polyethers, polyurethanes, and other biostable and biodegradable polymers.

Monomers suitable for use in the methods of the present invention includes monomers having the general structure of Formula 2

Formula 2 wherein $R^1$ is a polymerizable moiety including, but not limited to methacrylates, acrylates, lactones, $C_2$ to $C_{20}$ alkenyl, $C_2$ to $C_{20}$ alkynyl and $C_2$ to $C_{14}$ heteroatom substituted alkyl.

Polymer backbones suitable for use in the methods of the present invention include backbones selected from the group consisting of polyethers, vinyl polymers such as poly methacrylates, poly acrylates, polystyrene and poly(vinyl chloride), polycarbonate, polyurethane, polyesters and derivatives thereof.

The acrylate or methacrylate polymers comprise acrylic or methacrylic monomers including, but not limited to, methyl methacrylate, ethyl methacrylate, propyl methacrylate, butyl methacrylate, pentyl methacrylate, hexyl methacrylate, heptyl methacrylate, octyl methacrylate, dodecyl methacrylate, 2-(ethoxy ethyl methacrylate), glycidyl methacrylate, poly (ethylene glycol) methacrylate, methyl acrylate, ethyl acrylate, propyl acrylate, butyl acrylate, pentyl acrylate, hexyl acrylate, heptyl acrylate, octyl acrylate, dodecyl acrylate, 2-ethoxyethyl acrylate, glycidyl acrylate, poly(ethylene glycol) acrylate. In one embodiment, the methacrylate monomer is glycidyl methacrylate which has epoxide side chains. Non-acrylate monomers of the present invention include, but are not limited to, ε-caprolactone, polyethylene glycol (PEG), trimethylene carbonate, lactide, glycolide, N-acetyl 4-aza-caprolactone, cyclohexyl caprolactone, 4-tert-butyl caprolactone, the caprolactone of Formula 4, and their derivatives.

The polymers of the present invention include side chains wherein one or more of the side chains further comprise at least one secondary amine group. The secondary amine groups can be introduced either before (Reaction 1 in Scheme 1 producing Formula 3) or after (Reaction 2 in Scheme 1) monomer polymerization. In one embodiment, the secondary amines may be introduced through nucleophilic or electrophilic epoxide-opening reactions on either monomers or polymers. The general reaction is presented in Scheme 1, wherein $R^1$ is a polymerizable moiety including, but not limited to acrylates, methacrylates, lactones, $C_2$ to $C_{20}$ alkenyl and $C_2$ to $C_{20}$ alkynyl, and $R^2$ is a $C_1$ to $C_{10}$ straight chain alkyl, $C_3$ to $C_8$ cycloalkyl, $C_2$ to $C_{20}$ alkenyl, $C_2$ to $C_{2}$, alkynyl, $C_2$ to $C_{14}$ heteroatom substituted alkyl, $C_2$ to $C_{14}$ heteroatom substituted cycloalkyl, $C_1$ to $C_{10}$ multiple amine-containing hydrocarbons, $C_4$ to $C_{10}$ substituted aryls, or $C_4$ to $C_{10}$ substituted heteroatom substituted heteroaryls. $R^1$ and $R^2$ can be the same or different. Exemplary $C_1$-$C_{10}$ multiple amine-containing hydrocarbons include, but are not limited to, N-methylethylenediamine, N-methylpropylenediamine, N-methylbutylenediamine, N-ethylethylenediamine, N-ethylpropylenediamine, N-ethylbutylenediamine, N-benzylethylenediamine, N benzylpropylenediamine, N-benzylbutylenediamine, N-propylethylenediamine, N-propylpropylenediamine, and N-propylbutylenediamine, ethylenediamine, diethylenetriamine, triethylenetetramine, tetraethylenepentamine and pentaethylenehexamine.

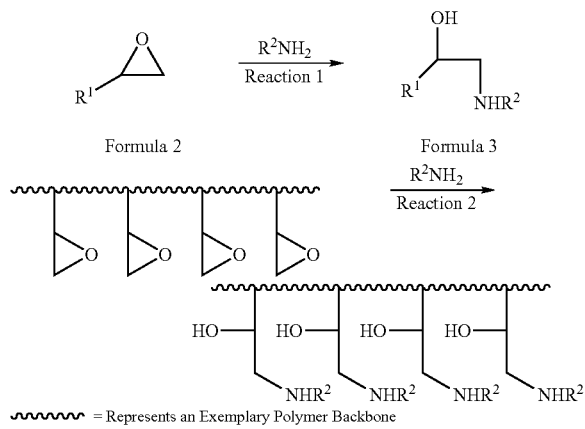

= Represents an Exemplary Polymer Backbone

The epoxides in the polymer side chains are synthesized by reactions including dehydration reactions, oxidization of alkenes, and ring closing reactions. An exemplary monomer having an epoxide-containing side chain is glycidyl methacrylate. The present invention also includes methods of synthesizing the epoxide side chains on monomers to prepare the monomers for polymerization. In one embodiment, alkene-containing polymerizable monomers are treated with dimethyldioxirane to yield the epoxide-containing side chain. In another embodiment, the alkene-containing monomer is 2-allyl caprolactone (Formula 4). The epoxidation of the alkene-containing monomers are performed either before polymerization of the monomers or after polymerization.

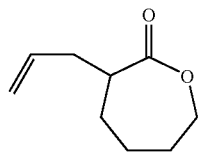

Formula 4

The alkene-containing monomers can be homopolymerized or copolymerized with different monomers. In one embodiment, 2-allyl caprolactone (Formula 4) is copolymerized with other lactones such as, but not limited to, glycolide, lactide, and other biocompatible lactones. The resulting copolymer is then epoxidized. The epoxidation reaction on the alkene-containing monomers or the alkene-containing polymers can be carried out with a number of reagents such as, but not limited to, dimethyldioxirane, mCPBA, metal oxides, peroxides, peracids, cyclic peroxides, and derivatives thereof. In another embodiment the 2-allyl caprolactone (Formula 4) is homopolymerized and the resultant polymer then epoxidated. Once the polymers having epoxide-containing side chains are synthesized, they are treated with primary amines to yield polymers having secondary amine side chains (as illustrated in Scheme 1). The resulting polymers having secondary side chains as depicted in the products of Reaction 2 (Scheme 1) can also be considered as amino alcohols.

The polymers of the present invention comprise at least one secondary amine per amine-bearing monomer unit. The secondary amines are introduced through nucleophilic attack of the amines on an electrophilic moiety on the monomer unit. The reactions introducing the amines through nucleophilic attack are optionally catalyzed. Catalysts useful in synthesizing the polymers of the present invention include but are not limited to $LiClO_4$, mineral acids, Bronsted acids, ion exchange resins, zeolites, oxophilic metals, proton sponges, buffer solutions, alkali earth metals, alkaline earth metals, transition metals, and organometallic compounds. In one embodiment of the present invention depicted in Formula 5, an amine is introduced on a polymer derived from glycidyl methacrylate (subunit a) and a methacrylate (subunit b) through nucleophilic attack on the epoxide. In Formulae 5 and 6, $R^3$ is a $C_1$ to $C_{20}$ straight chain alkyl, $C_5$ to $C_{10}$ cycloalkyl, alkoxy substituted $C_2$ to $C_{10}$ alkyl, or heteroatom substituted $C_2$ to $C_{10}$ alkyl or polyethylene glycol (PEG) (Reaction 3). In Formula 6, $R^2$ is a $C_1$ to $C_{10}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_1$ to $C_{10}$ multiple amine-containing hydrocarbons, $C_4$ to $C_{10}$ substituted aryl, or $C_4$ to $C_{10}$ substituted heteroatom substituted heteroaryl.

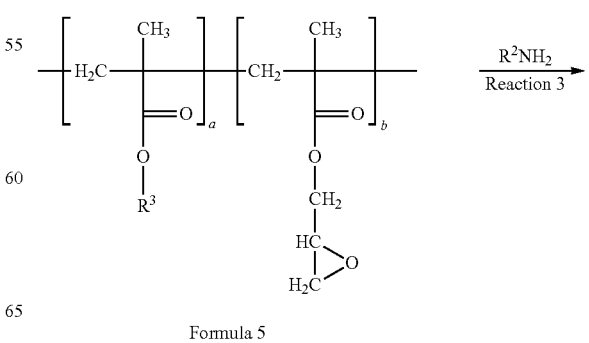

Formula 5

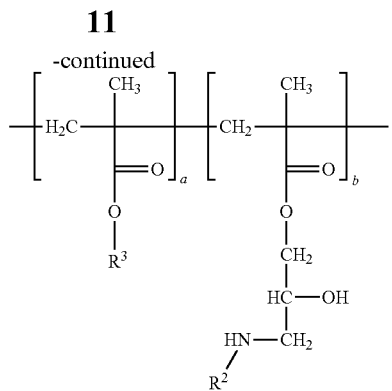

Formula 6

In one embodiment of the present invention, the a and b units of Formulae 5 and 6 are individually integers from 1 to 20,000. In additional embodiments, a is an integer ranging from 10 to 20,000; from 50 to 15,000; from 100 to 10,000; from 200 to 5,000; from 500 to 4,000; from 700 to 3,000; or from 1000 to 2000. In additional embodiments, b is an integer ranging from 10 to 20,000; from 50 to 15,000; from 100 to 10,000; from 200 to 5,000; from 500 to 4,000; from 700 to 3,000; or from 1000 to 2000.

The side chains can be synthetically fine tuned to provide controlled release of NO by choosing the appropriate amines for nucleophilic attack on the precursor polymers.

Non-acrylate polymers of the present invention include polyesters, polycarbonates, polyethers, polyurethanes, and other biostable or biodegradable polymers. In one embodiment of the present invention, the NO donating polymer is a polyester of Formula 9, wherein n is an integer from 0 to 4 and m is an integer from 1 to 20,000. The polyester of Formula 9 is synthesized from the epoxide of Formula 8 through a standard ring opening reaction with a primary amine. In Formula 9, $R^2$ is a $C_1$ to $C_{10}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_1$ to $C_{10}$ multiple amine-containing hydrocarbons, $C_4$ to $C_{10}$ substituted aryl or $C_4$ to $C_{10}$ substituted heteroatom substituted heteroaryl.

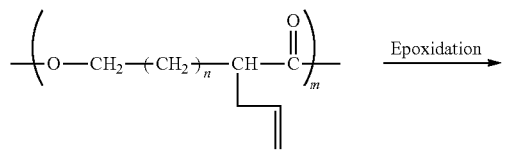

Formula 7

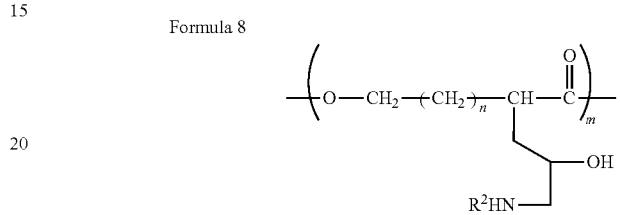

Formula 8

Formula 8

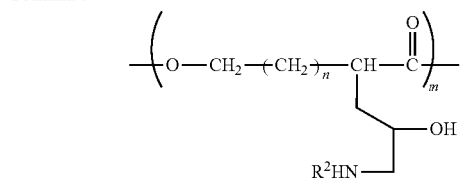

Formula 9

In one embodiment of Formulae 7, 8 and 9 of the present invention, m is an integer ranging from 1 to 20,000. In additional embodiments, m is an integer ranging from 10 to 19,000, from 200 to 17,000, from 400 to 15,000, from 500 to 14,000, from 600 to 13,000, from 700 to 12,000, from 800 to 11,000, from 900 to 12,000, from 1,000 to 11,000, from 1,100 to 10,000, from 1,200 to 9,000, from 1,300 to 8,000, from 1,400 to 7,000, from 1,500 to 6,000, from 1,600 to 5,000, from 1,600 to 4,000, from 1,700 to 3,000, from 1,800 to 2,000 or from 1,900 to 1,950. In another embodiment of Formulae 7, 8 and 9 of the present invention, n is an integer ranging from 0 to 4. In additional embodiments, n is 2 or 3.

The non-acrylic polymers of the present invention are not limited to homopolymers. In one embodiment of the present invention, copolymers of polyethers and polyesters are synthesized according to Formula 10 which undergoes the reactions described above to form the epoxide of Formula 11. The epoxide of Formula 11 is then treated with a primary amine to yield the polymer of Formula 12. In Formula 12, $R^2$ is a $C_1$ to $C_{10}$ straight chain alkyl, $C_3$ to $C_8$ cycloalkyl, $C_1$ to $C_{10}$ multiple amine-containing hydrocarbons, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_4$ to $C_{10}$ substituted aryl or $C_4$ to $C_{10}$ substituted heteroatom substituted heteroaryl. In Formula 12, n is an integer from 0 to 4, m is an integer from 1 to 20,000 and f is an integer from 1 to 20,000.

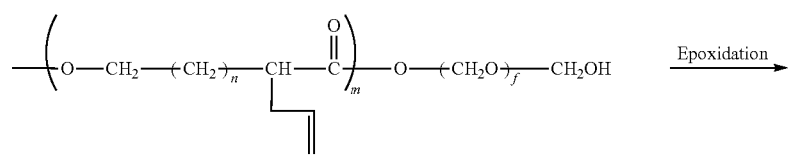

Formula 10

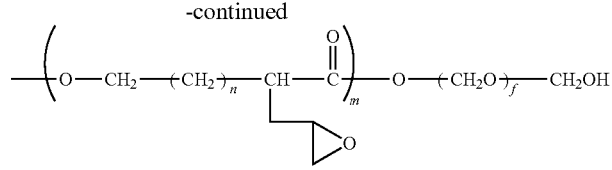

Formula 11

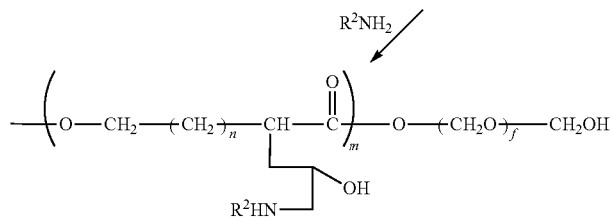

Formula 12

In one embodiment of Formulae 10, 11 and 12 of the present invention, m and f are individually integers from 1 to 20,000. In additional embodiments, m is an integer ranging from 10 to 19,000, from 200 to 17,000, from 400 to 15,000, from 500 to 14,000, from 600 to 13,000, from 700 to 12,000, from 800 to 11,000, from 900 to 12,000, from 1,000 to 11,000, from 1,100 to 10,000, from 1,200 to 9,000, from 1,300 to 8,000, from 1,400 to 7,000, from 1,500 to 6,000, from 1,600 to 5,000, from 1,600 to 4,000, from 1,700 to 3,000, from 1,800 to 2,000 or from 1,900 to 1,950. In additional embodiments, f is an integer ranging from 10 to 19,000, from 200 to 17,000, from 400 to 15,000, from 500 to 14,000, from 600 to 13,000, from 700 to 12,000, from 800 to 11,000, from 900 to 12,000, from 1,000 to 11,000, from 1,100 to 10,000, from 1,200 to 9,000, from 1,300 to 8,000, from 1,400 to 7,000, from 1,500 to 6,000, from 1,600 to 5,000, from 1,600 to 4,000, from 1,700 to 3,000, from 1,800 to 2,000 or from 1,900 to 1,950. In another embodiment of Formulae 10, 11 and 12 of the present invention, n is an integer ranging from 1 to 4. In additional embodiments, n is 2 or 3.

Physical properties of the polymers in the present invention can be fine tuned so that the polymers can optimally perform for their intended use. Properties that can be fine tuned, without limitation, include $T_g$, molecular weight (both $M_n$ and $M_w$), polydispersity index (PDI, the quotient of $M_w/M_n$), degree of elasticity and degree of amphiphlicity. In one embodiment of the present invention, the $T_g$ of the polymers range from about −10° C. to about 85° C. In still another embodiment of the present invention, the PDI of the polymers range from about 1.3 to about 4.0. In another embodiment of the present invention, the $T_g$ of the polymers ranges form about 0° C. to about 40° C. In still another embodiment of the present invention, the PDI of the polymers range from about 1.5 to about 2.5.

Implantable medical devices suitable for coating with the epoxide-derived NO-donating polymers of the present invention include, but are not limited to, vascular stents, stent grafts, urethral stents, bile duct stents, catheters, guide wires, pacemaker leads, bone screws, sutures and prosthetic heart valves. The polymers of the present invention are suitable for fabricating implantable medical devices. Medical devices which can be manufactured from the epoxide-derived NO-donating polymers of the present invention include, but are not limited to, vascular stents, stent grafts, urethral stents, bile duct stents, catheters, guide wires, pacemaker leads, bone screws, sutures and prosthetic heart valves.

The polymeric coatings of the present invention are intended for medical devices deployed in a hemodynamic environment and possess excellent adhesive properties. That is, the coating must be stably linked to the medical device surface. Many different materials can be used to fabricate the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the polymeric coatings made in accordance with the teachings of the present invention. Furthermore, the polymers of the present invention can be used to fabricate an entire medical device.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The epoxide-derived NO-donating polymeric coatings of the present invention can be applied to medical device surfaces, either primed or bare, in any manner known to those skilled in the art. Applications methods compatible with the present invention include, but are not limited to, spraying, dipping, brushing, vacuum-deposition, electrostatic spray coating, plasma coating, spin coating electrochemical coating, and others. Moreover, the epoxide derived NO-donating polymeric coatings of the present invention may be used with a cap coat. A cap coat as used herein refers to the outermost coating layer applied over another coating. A NO-donating polymer coating is applied over the primer coat. Then, a polymer cap coat is applied over the epoxide derived NO-donating polymeric coating. The cap coat may optionally serve as a diffusion barrier to control the NO release. The cap coat may be merely a biocompatible polymer applied to the surface of the sent to protect the stent and have no effect on the NO release rates.

The epoxide-derived NO-donating polymers of the present invention are also useful for the delivery and controlled release of drugs. Drugs that are suitable for release from the polymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention the drugs controllably released include, but are not limited to, macrolide antibiotics including FKBP-12 binding agents. Exemplary drugs of this class include sirolimus (rapamycin) (Formula 2), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487 now U.S. Pat No. 7,271,177) and zolimus (ABT-578; see U.S. Pat. Nos. 6,015,815 and 6,329,386) (Formula 1). Additionally, and other rapamycin hydroxyesters as disclosed in U.S. Pat. No. 5,362,718 may be used in combination with the polymers of the present invention. The entire contents of all of preceding patents and patent applications are herein incorporated by reference for all they teach related to FKBP-12 binding compounds and the derivatives.

EXAMPLES

The following non limiting examples provide methods for the synthesis of exemplary polymers according to the teachings of the present invention.

Example 1

Synthesis of Glycidyl Methacrylate/Hexyl Methacrylate Copolymer

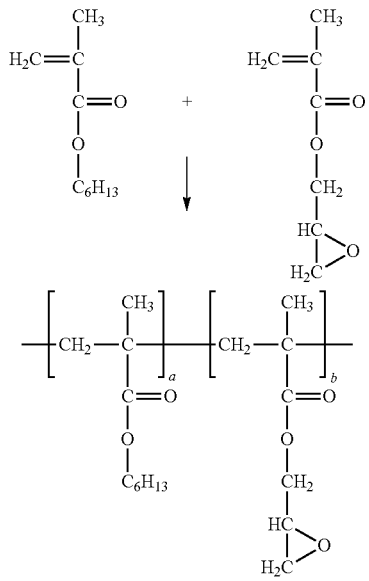

Glycidyl methacrylate (9.02 g), n-hexyl methacrylate (21.03 g), 1,4-dioxane (59.98 g) and AIBN (240 mg) were mixed in a 120 mL bottle, which was sealed and purged with nitrogen for 30 minutes. The bottle was heated at 60° C. for 3 hours with stirring in an oil bath. The polymer was purified by repeated precipitation (3×) in methanol from dichloromethane solution. After drying in a vacuum oven at 45° C. overnight, a copolymer of n-hexyl methacrylate (56 mol %) and glycidyl methacrylate (44 mol %) was obtained according to $^1$H NMR. The polymer has a weight average molecular weight of 232240 and PDI of 2.0 according to GPC (THF, 35C and polystyrene standard). The $T_g$ of the polymer is 28.8° C. as measured with DSC at a heating rate of 20° C./min on the second heat.

Example 2

Converting the Epoxide Groups to Second Amine Groups in the Side Chains

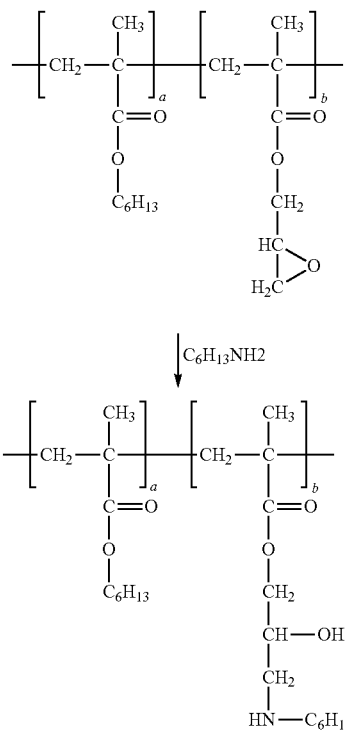

In this example, 1.0 g of polymer from example 1 was dissolved in 3 mL THF in a bottle. Then 14.5 mL of 1-hexylamine was added. The bottle was sealed and heated in an oil bath at 50° C. overnight. NMR indicated that the epoxide was consumed. The resulting polymer was purified by repeated precipitation (3×) into hexanes/ethyl acetate (v/v 80/20) from THF solution. The polymer was dried in vacuum at room temperature overnight.

Example 3

Convert Secondary Amine Functional Polymer to Diazeniumdiolated Polymer

About 1 mg of polymer (N27) from Example 2 was dipped coated onto ¼ inch stainless steel coupon from THF solution. The coupon was dried in vacuum and the coated polymer was dry diazeniumdiolated under 80 psi NO for 3 days. The coupon was incubated in PBS (pH 7.4) buffer tube and the nitric oxide released was detected with a nitric oxide analyzer (GE Analytical Instrument 2801). The diazeniumdiolated polymer showed initial release rate of 5.78 pmol/min/mg and released 1.49 nmol/mg of nitric oxide in 18.5 hours.

Example 4

Converting the Epoxide Groups to Multiple Second Amine Groups in the Side Chains

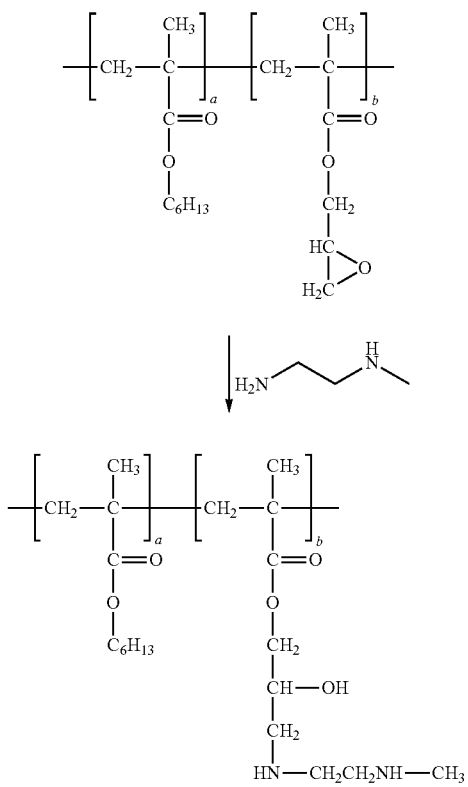

Precursor copolymer of hexyl methacrylate (64 mol %) and glycidyl methacrylate (36 mol %) was similarly prepared as in Example 1. In this example, 2.03 gram of the precursor polymer was dissolved in 4 mL THF and mixed with 19.2 mL of N-methylethylenediamine in a bottle. The bottle was sealed and heated in an oil bath at 60° C. for 22 hours. The polymer was purified by repeated precipitation (3×) in hexanes from THF solution. The polymer was dried in vacuum at room temperature overnight.

Example 5

About 1 mg of polymer (N47) from example 2 was dipped coated onto ¼ inch stainless steel coupon from THF solution. The coupon was dried in vacuum and the coated polymer was dry diazeniumdiolated under 80 psi NO for 3 days. The coupon was incubated in PBS (pH 7.4) buffer tube and the nitric oxide released was detected with a nitric oxide analyzer (GE Analytical Instrument 2801). The diazeniumdiolated polymer showed initial release rate of 401 pmol/min/mg and released 110 nmol/mg of nitric oxide in 23.5 hours.

Example 6

Converting the epoxide groups to multiple amine groups in the side chains

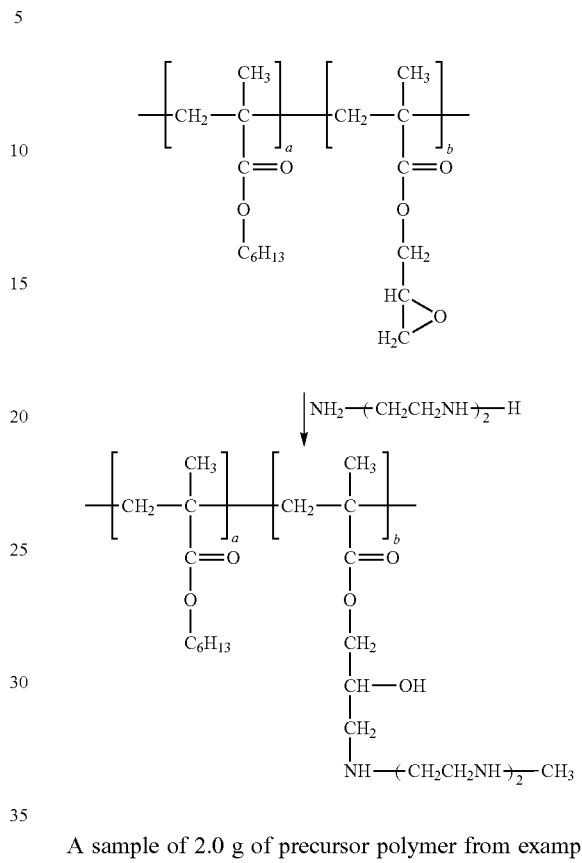

A sample of 2.0 g of precursor polymer from example 4 was dissolved in 8 mL THF. Separately another solution was prepared by mixing 23.9 mL of diethylenetriamine with 12 mL of THF. The polymer solution was added to the diethylenetriamine solution drop wise under agitation. The mixture was heated at 50° C. in an oil bath for three days. The resulting polymer was purified by precipitation into deionized water from THF solution. The $^1$H NMR spectrum in $d_4$-methanol indicated the disappearance of the epoxide functional groups and the appearance of new peaks at around 2.7 ppm corresponding to the $NCH_2$ groups.

Example 7

About 1 mg of polymer (N59) from example 6 was dip-coated onto ¼ inch stainless steel coupon from THF solution and diazeniumdiolated under 80 psi NO pressure for 3 days. The coupon was incubated in PBS (pH 7.4) buffer tube and the NO released was detected with a NO analyzer (GE Analytical Instrument 280i). The diazeniumdiolated polymer showed an initial release rate of 635 pmol/min/mg and released 141 nmol/mg of NO in 122.1 hours as shown in the nitric oxide release curve of FIG. 1.

Example 8

Manufacture of Stents from Epoxide-Derived NO-Donating Polymers

For exemplary, non-limiting, purposes a vascular stent will be described. A biodegradable NO-donating polymer is heated until molten in the barrel of an injection molding machine and forced into a stent mold under pressure. After the molded polymer (which now resembles and is a stent) is cooled and solidified the stent is removed from the mold. In one embodiment of the present invention the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube. In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer $T_g$ and the melting temperature of the polymer blend for a time period between about five minutes and about 18 hours in air, an inert atmosphere or under vacuum. The stent is then allowed to cool and is then cut.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of providing a polymer, the method comprising:
    (a) providing a polymer having epoxide pendant groups;
    (b) reacting said polymer with an amine compound having the general formula $R^2$—$NH_2$;
        wherein the molar ratio of amine compound to epoxide groups of the epoxide-containing polymer is at least 39:1 and no greater than 48:1;
    wherein $R^2$ is selected from the group consisting of $C_1$ to $C_{20}$ straight chain alkyls, $C_3$ to $C_8$ cycloalkyls, $C_2$ to $C_{20}$ alkenyls, $C_2$ to $C_{20}$ alkynyls, $C_2$ to $C_{14}$ heteroatom substituted alkyls, $C_2$ to $C_{14}$ heteroatom substituted cycloalkyls, $C_1$ to $C_{10}$ multiple amine containing-hydrocarbons, $C_4$ to $C_{10}$ substituted aryls and $C_4$ to $C_{10}$ substituted heteroatom substituted heteroaryls, under conditions wherein a secondary amine is formed; and
    (c) reacting said secondary amine with NO under pressure to form a diazeniumdiolate thereof.

2. The method according to claim 1 wherein said reaction step (b) further comprises a catalyst.

3. The method according to claim 2 wherein said catalyst is selected from the group consisting of $LiClO_4$, mineral acids, Bronsted acids, ion exchange resins, zeolites, oxophilic metals, proton sponges, buffer solutions, alkali earth metals, alkaline earth metals, transition metals, and organometallic compounds.

4. The method according to claim 1 wherein $R^2-NH_2$ is selected from the group consisting of N-methylethylenediamine, N-methylpropylenediamine, N-methylbutylenediamine, N-ethylethylenediamine, N-ethylpropylenediamine, N-ethylbutylenediamine, N-benzylethylenediamine, N-benzylpropylenediamine, N-benzylbutylenediamine, N-propylethylenediamine, N-propylpropylenediamine, and N-propylbutylenediamine, ethylenediamine, diethylenetriamine, triethylenetetramine, tetraethylenepentamine and pentaethylenehexamine.

5. The method according to claim 1 wherein said polymer is selected from the group consisting of polyethers, vinyl polymers of poly methacrylates, polyacrylates, polystyrene and poly(vinyl chloride), polycarbonate, polyurethane and polyesters.

6. The method according to claim 5 wherein said polymer is comprised of monomers selected from the group consisting of methyl methacrylate, ethyl methacrylate, propyl methacrylate, butyl methacrylate, pentyl methacrylate, hexyl methacrylate, heptyl methacrylate, octyl methacrylate, dodecyl methacrylate, 2-(ethoxy ethyl methacrylate), glycidyl methacrylate, poly(ethylene glycol) methacrylate, methyl acrylate, ethyl acrylate, propyl acrylate, butyl acrylate, pentyl acrylate, hexyl acrylate, heptyl acrylate, octyl acrylate, dodecyl acrylate, 2-ethoxyethyl acrylate, glycidyl acrylate, poly(ethylene glycol) acrylate, ε-caprolactone, polyethylene glycol (PEG), trimethylene carbonate, lactide, glycolide, N-acetyl 4-aza- caprolactone, cyclohexyl caprolactone, 4-tert-butyl caprolactone and the caprolactone of Formula 4.

7. The method of claim 1 wherein reacting a polymer having epoxide pendant groups with a compound having the general formula $R^2-NH_2$ occurs in THF solution.

8. A method of providing a nitric oxide (NO)-donating polymer, the method comprising:
(a) providing a polymer having epoxide pendant groups;
(b) reacting said epoxide pendant groups on said polymer with a primary amine under conditions effective to ring open the epoxide and form side chains comprising secondary amine groups; wherein the molar ratio of the primary amine compound to epoxide groups of the epoxide-containing polymer is at least 39:1 and no greater than 48:1; and
(c) reacting said secondary amine groups with NO under pressure to form a diazeniumdiolate thereof, thereby forming an NO-donating polymer;
wherein said primary amine is of the formula $R^2-NH_2$, wherein $R^2$ is selected from the group consisting of $C_1$ to $C_{20}$ straight chain alkyls, $C_3$ to $C_8$ cycloalkyls, $C_2$ to $C_{20}$ alkenyls, $C_2$ to $C_{20}$ alkynyls, $C_2$ to $C_{14}$ heteroatom substituted alkyls, $C_2$ to $C_{14}$ heteroatom substituted cycloalkyls, $C_1$ to $C_{10}$ multiple amine containing-hydrocarbons, $C_4$ to $C_{10}$ substituted aryls and $C_4$ to $C_{10}$ substituted heteroatom substituted heteroaryls.

9. The method according to claim 8 wherein reacting a polymer having epoxide pendant groups with a primary amine occurs in THF solution.

10. The method according to claim 8 wherein the amine is selected from the group consisting of N-methylethylenediamine, N-methylpropylenediamine, N-methylbutylenediamine, N-ethylethylenediamine, N-ethylpropylenediamine, N-ethylbutylenediamine, N-benzylethylenediamine, N-benzylpropylenediamine, N-benzylbutylenediamine, N-propylethylenediamine, N-propylpropylenediamine, and N-propylbutylenediamine, ethylenediamine, diethylenetriamine, triethylenetetramine, tetraethylenepentamine and pentaethylenehexarnine.

11. The method according to claim 8 wherein said polymer is selected from the group consisting of polyethers, vinyl polymers of poly methacrylates, polyacrylates, polystyrene and poly(vinyl chloride), polycarbonate, polyurethane and polyesters.

12. The method according to claim 11 wherein said polymer is comprised of monomers selected from the group consisting of methyl methacrylate, ethyl methacrylate, propyl methacrylate, butyl methacrylate, pentyl methacrylate, hexyl methacrylate, heptyl methacrylate, octyl methacrylate, dodecyl methacrylate, 2-(ethoxy ethyl methacrylate), glycidyl methacrylate, poly(ethylene glycol) methacrylate, methyl acrylate, ethyl acrylate, propyl acrylate, butyl acrylate, pentyl acrylate, hexyl acrylate, heptyl acrylate, octyl acrylate, dodecyl acrylate, 2-ethoxyethyl acrylate, glycidyl acrylate, poly(ethyiene glycol) acrylate, ε-caprolactone, polyethylene glycol (PEG), trimethylene carbonate, lactide, glycolide, N-acetyl 4-aza- caprolactone, cyclohexyl caprolactone, 4-tert-butyl caprolactone and the caprolactone of Formula 4.

13. The method according to claim 8 wherein said reacting step (b) further comprises a catalyst.

14. The method according to claim 13 wherein said catalyst is selected from the group consisting of $LiClO_4$, mineral acids, Bronsted acids, ion exchange resins, zeolites, oxophilic metals, proton sponges, buffer solutions, alkali earth metals, alkaline earth metals, transition metals, and organometallic compounds.

* * * * *